US011160971B2

(12) United States Patent
Sharma et al.

(10) Patent No.: US 11,160,971 B2
(45) Date of Patent: *Nov. 2, 2021

(54) NEUROSLEEVE FOR CLOSED LOOP EMG-FES BASED CONTROL OF PATHOLOGICAL TREMORS

(71) Applicant: Battelle Memorial Institute, Columbus, OH (US)

(72) Inventors: Gaurav Sharma, Lewis Center, OH (US); Patrick Ganzer, Columbus, OH (US)

(73) Assignee: BATTELLE MEMORIAL INSTITUTE

( * ) Notice: Subject to any disclaimer, the term of this patent is extended or adjusted under 35 U.S.C. 154(b) by 0 days.

This patent is subject to a terminal disclaimer.

(21) Appl. No.: 17/002,135

(22) Filed: Aug. 25, 2020

(65) Prior Publication Data

US 2020/0406022 A1 Dec. 31, 2020

Related U.S. Application Data

(63) Continuation of application No. PCT/US2020/039802, filed on Jun. 26, 2020.

(60) Provisional application No. 62/868,158, filed on Jun. 28, 2019.

(51) Int. Cl.
*A61N 1/04* (2006.01)
*A61N 1/36* (2006.01)

(52) U.S. Cl.
CPC ......... *A61N 1/0452* (2013.01); *A61N 1/0456* (2013.01); *A61N 1/0484* (2013.01); *A61N 1/36031* (2017.08)

(58) Field of Classification Search
CPC .. A61N 1/0452; A61N 1/0456; A61N 1/0484; A61N 1/36014
See application file for complete search history.

(56) References Cited

U.S. PATENT DOCUMENTS

| 9,452,287 B2 * | 9/2016 | Rosenbluth ............ A61N 1/025 |
| 2008/0288020 A1 | 11/2008 | Einav et al. |
| 2015/0290451 A1 * | 10/2015 | Bouton ................ A61N 1/0484 607/48 |

(Continued)

FOREIGN PATENT DOCUMENTS

| EP | 2801389 A1 | 11/2014 |
| WO | WO 2014089266 A2 | 6/2014 |

(Continued)

OTHER PUBLICATIONS

International Search Report dated Oct. 16, 2020 from PCT/US2020/039802.

*Primary Examiner* — Alyssa M Alter
(74) *Attorney, Agent, or Firm* — Fay Sharpe LLP

(57) ABSTRACT

A tremor suppression device includes a garment wearable on an anatomical region and including electrodes contacting the anatomical region when the garment is worn on the anatomical region, and an electronic controller configured to: detect electromyography (EMG) signals as a function of anatomical location and time using the electrodes; identify tremors as a function of anatomical location and time based on the EMG signals; and apply neuromuscular electrical stimulation (NMES) at one or more anatomical locations as a function of time using the electrodes to suppress the identified tremors.

6 Claims, 2 Drawing Sheets

(56) References Cited

U.S. PATENT DOCUMENTS

| | | |
|---|---|---|
| 2015/0306373 A1 | 10/2015 | Bouton et al. |
| 2018/0081439 A1 | 3/2018 | Daniels |
| 2019/0142339 A1 | 5/2019 | Thommandram et al. |
| 2020/0405188 A1* | 12/2020 | Sharma ................ A61B 5/1101 |

FOREIGN PATENT DOCUMENTS

| | | |
|---|---|---|
| WO | WO 2014113813 A1 | 7/2014 |
| WO | WO 2018098046 A2 | 5/2018 |
| WO | WO 2019126080 A1 | 6/2019 |

\* cited by examiner

NEUROSLEEVE FOR CLOSED LOOP EMG-FES BASED CONTROL OF PATHOLOGICAL TREMORS

CROSS-REFERENCE TO RELATED APPLICATIONS

This application is a continuation of PCT Application No. PCT/US2020/039802, filed on Jun. 26, 2020, which claims priority to U.S. Provisional Patent Application Ser. No. 62/868,158, filed on Jun. 28, 2019, which is incorporated by reference in its entirety.

BACKGROUND

The following relates to the neuromuscular tremor control arts, RF transmitter arts, RF receiver arts, RF transceiver arts, broadband RF transmitter, receiver, and/or transceiver arts, RF communications arts, and related arts.

Current treatments for pathological tremors (involuntary muscle tremors due to an underlying disease such as Parkinson's disease, essential tremor disorder, or so forth) are not effective in about one-quarter of the population. Tremor movements that can have a large disabling impact include elbow flexion/extension, forearm pronation/supination, and wrist flexion/extension. Current biomechanical loading-based methods for tremor suppression are not effective as this type of therapy often leads to distal-to-proximal migration of tremors. Current FES-based tremor suppression technologies cannot alleviate pronation/supination tremors due to difficulty in selectively targeting muscles.

Certain improvements are disclosed herein.

BRIEF SUMMARY

In accordance with some illustrative embodiments disclosed herein, a tremor suppression device includes a garment wearable on an anatomical region and including electrodes contacting the anatomical region when the garment is worn on the anatomical region, and an electronic controller configured to: detect electromyography (EMG) signals as a function of anatomical location and time using the electrodes; identify tremors as a function of anatomical location and time based on the EMG signals; and apply neuromuscular electrical stimulation (NMES) at one or more anatomical locations as a function of time using the electrodes to suppress the identified tremors. In some embodiments the electronic processor is configured to identify tremors by operations including spectral filtering the EMG signals to remove frequency components corresponding to voluntary motion. In some embodiments the garment further includes at least one inertial motion unit (IMU) and the electronic processor is configured to identify tremors further based on an orientation of the anatomical region determined using the IMU. In some embodiments the electronic processor is configured to apply the NMES by operations including: determining tremor suppressing NMES at one or more anatomical locations as a function of time based on the identified tremors and an anatomy-specific tremor migration model; and applying the determined tremor suppressing NMES using the electrodes. In some embodiments the electronic processor is configured to apply the NMES by operations including: determining a tremor migration rate and direction based on a rate of change in anatomical location of the identified tremors as a function of time; determining tremor suppressing NMES at one or more anatomical locations as a function of time based on the identified tremors and the determined tremor migration rate and direction; and applying the determined tremor suppressing NMES using the electrodes. In some embodiments the electronic processor is configured to apply the NMES by operations including: classifying the identified tremors based on spectral analysis of the EMG signals; determining tremor suppressing NMES at one or more anatomical locations as a function of time based on the identified tremors and their classifications; and applying the determined tremor suppressing NMES using the electrodes. In some embodiments the garment is a sleeve and the anatomical region is an arm, a leg, a wrist, an ankle, an arm and a wrist, or a leg and an ankle. In some embodiments the anatomical region is an arm, a leg, a wrist, an ankle, a hand, a foot, an arm and a wrist, a leg and an ankle, an arm and a wrist and a hand, a leg and an ankle and a foot, a wrist and a hand, or an ankle and a foot. In some embodiments the electrodes comprise electrogel discs.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

DETAILED DESCRIPTION

Some illustrative embodiments disclosed herein comprise a wearable myoelectric-enabled neuromuscular electrical stimulation (NMES) sleeve providing closed-loop control to discriminate between voluntary motion and tremor-induced motion and to suppress tremors with selective NMES stimulation of muscles, thereby providing suppression or attenuation of mild, moderate and severe tremors. In some variant embodiments, such an NMES sleeve is used in combination with vagus nerve stimulation (VNS) in conjunction with motion to suppress tremors or spasticity.

Figure 1:
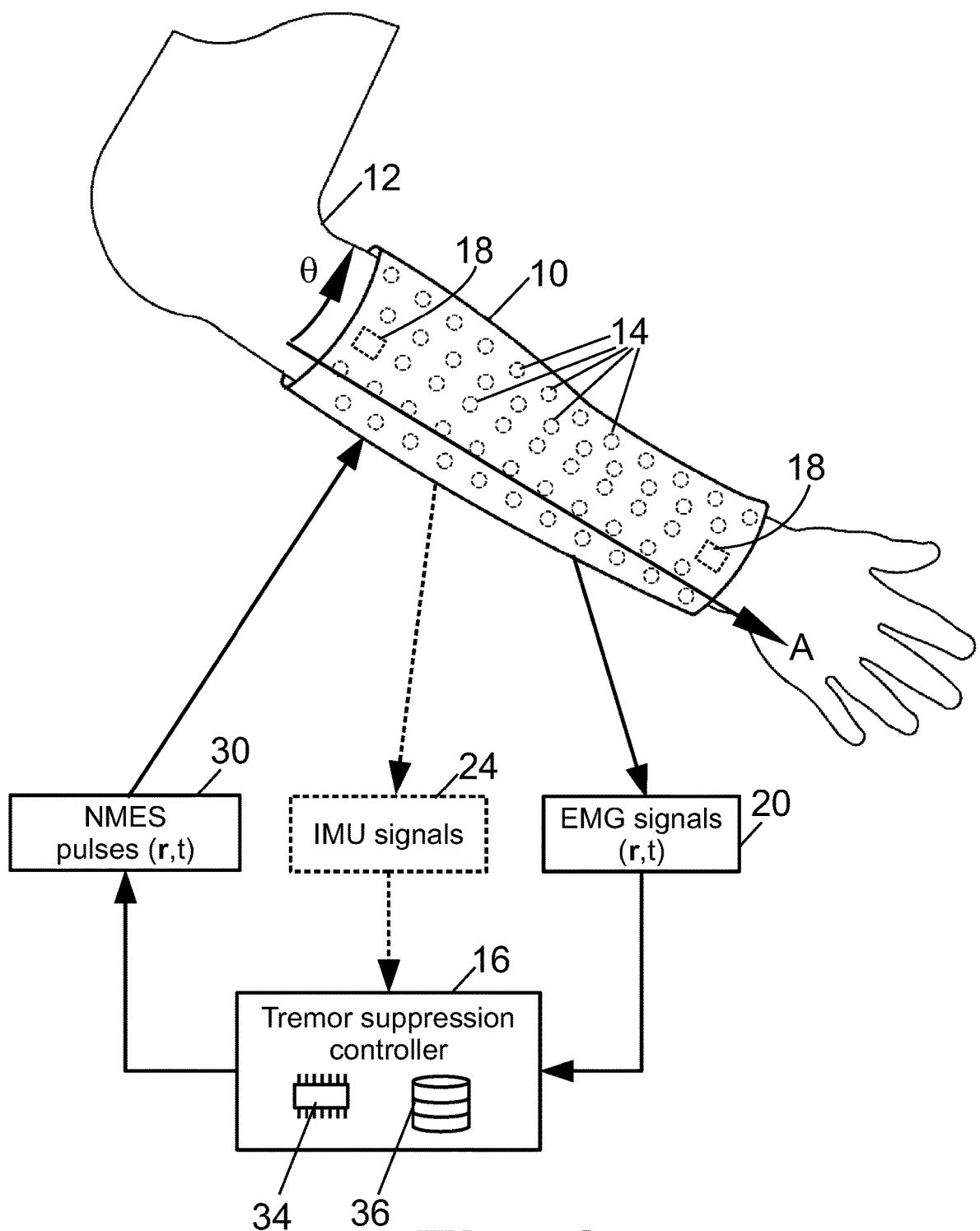
FIG. 1 diagrammatically illustrates a tremor suppression device.

With reference to FIG. 1, a garment 10 is wearable on an anatomical region 12, and includes electrodes 14 contacting the anatomical region 12 when the garment is worn on the anatomical region. The illustrative garment is a sleeve 10 worn on an arm 12. More generally, the garment may be made of a cloth, textile, leather, polyester, or other material, and is sized and shaped to be worn on the anatomical region for which tremor suppression therapy is to be provided. For example, the garment may be a sleeve that is sized and shaped to be worn on an arm, a leg, a wrist, an ankle, an arm and a wrist, or a leg and an ankle. The sizing is suitably patient-specific to account for different anatomies of different patients, or the garment may be designed to be adjustable for differences between patients—for example, the sleeve could employ a wrap-around arrangement with Velcro to be adjustably wrapped around arms of different diameters. In other examples, the anatomical region may be an arm, a leg, a wrist, an ankle, a hand, a foot, an arm and a wrist, a leg and an ankle, an arm and a wrist and a hand, a leg and an ankle and a foot, a wrist and a hand, or an ankle and a foot. Suitable garments for a hand would include, for example, a glove or mitten. Suitable garments for a foot would include, for example, a sock or boot. The glove, mitten, sock, or boot can be extended over the wrist or ankle to provide a garment for a wrist and hand or for an ankle and foot, or further extended to provide a garment for an arm and wrist and hand or for a leg and ankle and foot. These are merely non-limiting illustrative examples. The electrodes 14 are disposed on the inside of the garment 10 so as to contact the skin of the anatomical region 12 (FIG. 1 illustrates the garment 10 as transparent so as to reveal the underlying electrodes 14, but more typically the garment will be translucent or opaque), and are connected by wires (possibly woven into the garment), circuitry of flexible printed circuit boards, and/or so forth to an electrical connector (not shown) that connects with an electronic tremor suppression controller 16. Alternatively, the electronic tremor suppression controller 16 can be integrated with the garment 10, for example as a compact electronics package that is sewn onto or otherwise attached to the garment 10, and the wires, printed circuitry, or the like connects the electrodes 14 directly with the attached electronic tremor suppression controller 16. The electrodes 14 are designed to provide good electrical contact with the skin of the anatomical region 12. For example, the electrodes 14 may be electrogel discs. Optionally, the garment may further include at least one Inertial Motion Unit (IMU) 18 (illustrative FIG. 1 shows two IMUs 18, one near each end of the illustrative sleeve garment 10). The IMUs 18 may, for example, be accelerometers, gyroscopes, or the like.

By way of further non-limiting illustration, some suitable embodiments of the garment 10 wearable on the anatomical region 12 and including electrodes 14 contacting the anatomical region when the garment is worn on the anatomical region are described in Bouton et al., U.S. Pat. No. 9,884,178 issued Feb. 6, 2018 and Bouton et al., U.S. Pat. No. 9,884,179 issued Feb. 6, 2018, both of which are incorporated herein by reference in their entireties.

The term "anatomical location" is used herein in describing operation of the tremor suppression device. The anatomical location is defined with respect to the anatomical region 12, and each electrode 14 of the array of electrodes 14 of the garment 10 worn on the anatomical region 12 has a corresponding anatomical location. The anatomical region can be identified using a suitable coordinate system. The illustrative example of FIG. 1 employs an anatomical coordinate system with an axial coordinate A and an azimuthal coordinate θ. The anatomical location (denoted herein as r) of any particular electrode 14 on the anatomical region 12 is given by its axial and azimuthal coordinates, that is, r=(A,θ). This provides a way to specify the anatomical location with high spatial resolution. Some embodiments may not require such high spatial resolution—in such cases, the anatomical location may be given by a designation such as "upper wrist location", "lower wrist location", or so forth, or by designation of a particular underlying muscle, such as a designated flexor muscle. The association of a particular electrode 14 with a particular anatomical location may be inherent in the design of the garment 10 (for example, if the garment is a glove then there is substantially no flexibility as regarding how the glove fits onto the hand (which is the anatomical region in this case) so that each electrode is inherently in a known anatomical location when the glove is placed onto the hand. In other embodiments, there may be enough variability as to how the garment 10 fits onto the anatomical region 12 so that some alignment is appropriate. For example, illustrative sleeve 10 might be worn in various angular positions in the azimuthal (θ) direction. In such cases, suitable garment positional alignment may be determined by the person fitting the garment onto the patient, and the positional alignment information is then input to the electronic tremor suppression controller 16. In another approach, the garment may have some positioning index information, for example the illustrative sleeve 10 could include an alignment mark near the wrist end that is to be aligned with the medial vein of the forearm.

Figure 2:
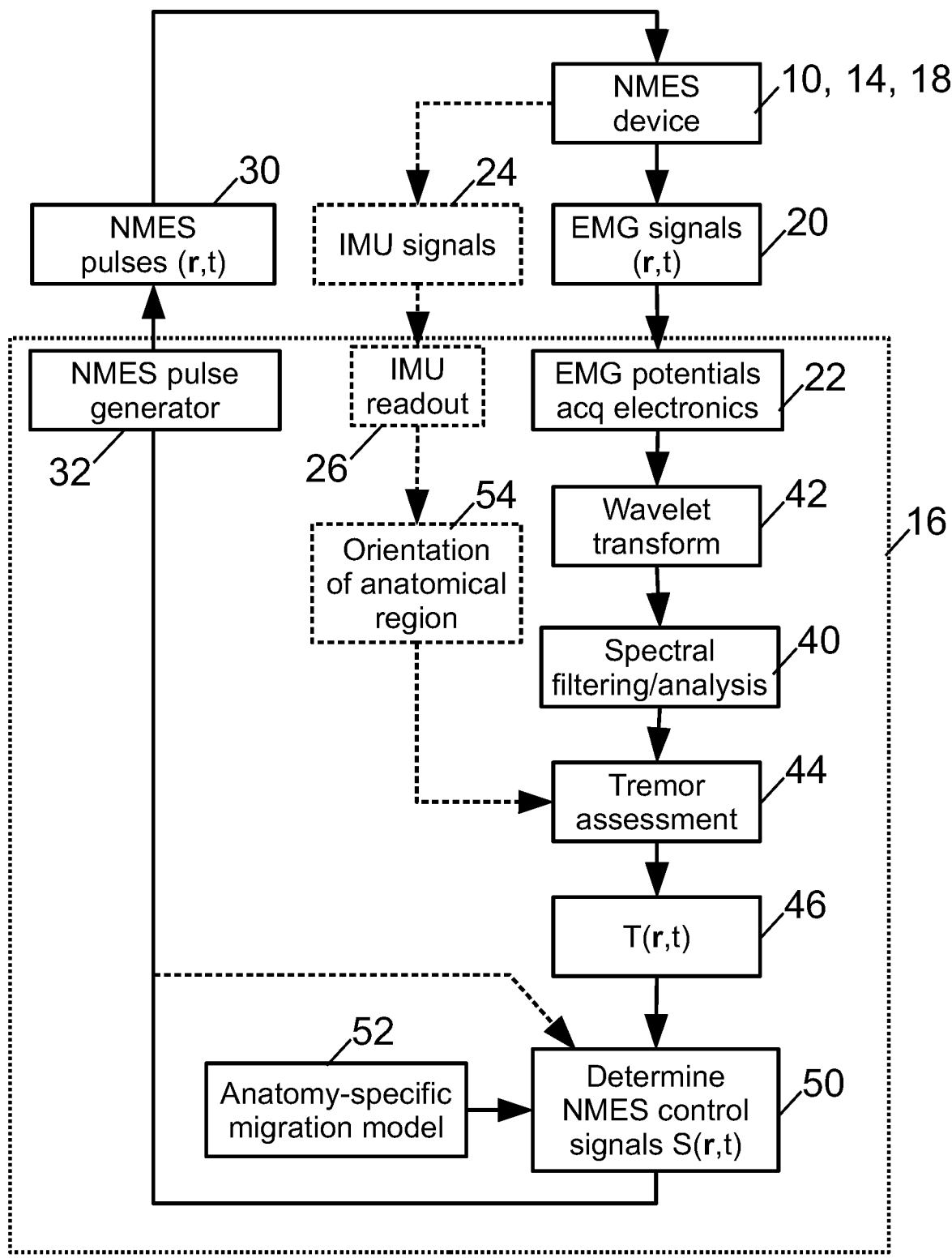
FIG. 2 diagrammatically illustrates a tremor suppression process suitably performed by the tremor suppression processor of the device of FIG. 1.

With continuing reference to FIG. 1 and with further reference to FIG. 2, the electronic tremor suppression controller 16 is configured to detect electromyography (EMG) signals 20 as a function of anatomical location (r) and time (t) using the electrodes 14. Typically, the electrodes 14 are surface electrodes (e.g. electrogel discs) and measure surface EMG signals 20; however, use of needle electrodes or the like for measuring intramuscular EMG signals is also contemplated. The EMG signal measurements are potential difference measurements between pairs of electrodes 14 acquired using any suitable voltmeter circuit or other EMG potentials acquisition electronics 22. The anatomical location (r) of an EMG signal is suitably designated by the employed electrodes, e.g. as a midpoint between the anatomical locations of the electrodes of the pair. The EMG signals 20 also vary as a function of time (t) in accord with various muscle contraction/relaxation activity. Hence, the EMG signals may be designated as EMG(r,t). The EMG potentials acquisition electronics 22 preferably further include analog-to-digital (ND) circuitry to convert the EMG signals 20 to digital signal values.

Optionally, the electronic tremor suppression controller 16 is further configured to receive IMU signals 24 with suitable IMU readout circuitry 26. In one contemplated embodiment, the IMUs 18 are commercially available triple-axis accelerometers that output the IMU signals 24 as digital signals, and the IMU readout circuitry 26 is designed to read the digital accelerometer signals.

The electronic tremor suppression controller 16 is further configured to generate neuromuscular electrical stimulation (NMES) pulses 30 using an NMES pulse generator 32. By way of some non-limiting illustrative embodiments, some suitable NMES pulse waveforms may include monophasic and biphasic pulses with a voltage between 80 to 300 Volts inclusive or higher. In one example, the NMES pulse waveform is a monophasic pulse with a peak current of 0-20 mA which is modulated to vary strength of muscle contraction, frequency of 50 Hz, and a pulse width duration of 500 ms. Again, these are merely non-limiting illustrative examples.

With particular reference to FIG. 1, the electronic tremor suppression controller 16 further includes an electronic processor 34, such as a microprocessor or microcontroller (or two or more microprocessors or microcontrollers, e.g. a quad-CPU) and a non-transitory storage medium 36 (which again may comprise two or more media, possibly of different types). In some advantageous embodiments, the non-transitory storage medium 36 comprises a flash memory, solid-state drive (SSD), or other non-volatile electronic memory, although other types of media such as magnetic (e.g. a hard disk drive), optical (e.g. an optical disk) or so forth are additionally or alternatively contemplated. The non-transitory storage medium 36 stores firmware or software comprising instructions that are readable and executable by the electronic processor 34 to perform disclosed tremor suppression control operations including identifying tremors as a function of anatomical location (r) and time (t) based on the EMG signals; and applying NMES at one or more anatomical locations as a function of time using the electrodes 14 to suppress the identified tremors. Advantageously, because the garment 10 is spatially extended (e.g. running from the wrist to the elbow in the illustrative example of FIG. 1, or in other embodiments further covering the wrist and/or elbow) the tremor suppression device can deliver therapeutic (i.e., tremor suppressing) NMES at specific anatomical locations at specific times. In particular, the disclosed tremor suppression device can suppress tremors in the presence of tremor migration.

With particular reference to FIG. 2, the detected EMG signals as a function of anatomical location and time are analyzed to identify tremors as a function of anatomical location and time. This identification should exclude voluntary motions. One way to do so is to leverage the observation that frequencies of EMG signals associated with voluntary motions are usually 1 Hz or lower; whereas, EMG signals associated with tremors are usually 2 Hz or higher in frequency. Hence, in some embodiments, spectral filtering of the EMG signals is used to remove frequency components corresponding to voluntary motion. For example, a high-pass or band-pass filter can be applied with a lower cutoff frequency of between 1 Hz and 2 Hz inclusive.

Optionally, tremors may be classified on the basis of a frequency analysis. Most voluntary movements generate EMG signals at low (<1 Hz) frequency, while the EMG frequencies of tremors varies from rest tremor (3-6 Hz), postural tremor (4-12 Hz), kinetic/intention tremor (2-5 Hz or 7 Hz). These filtering operations for removal of EMG signals associated with voluntary movements and optional tremor classification are represented in FIG. 2 by the spectral filtering/analysis operation 40. In some embodiments, the EMG signals are optionally initially converted to a wavelets representation using a wavelets transform 42.

The resulting processed and filtered EMG signals are (at least predominantly) associated with tremors, and are then processed by a tremor assessment operation 44 to identify (and optionally classify) tremors. For example, a tremor may be identified as a spatially localized region r which, over some time, exhibits EMG signals at the tremor frequency range above some minimum threshold amplitude. Such tremors 46 are denoted herein as tremors $T(r,t)$. In embodiments employing a high spatial resolution anatomical coordinate system such as the illustrative $(A,\theta)$ anatomical coordinate system of FIG. 1, $T(r,t)$ can be represented at high spatial resolution by denoting the tremor anatomical position r in $(A,\theta)$ coordinates. In other embodiments, tremors $T(r,t)$ are given with the anatomical position r more coarsely designated by a designation such as "upper wrist location", "lower wrist location", or so forth, or by designation of a particular underlying muscle, such as a designated flexor muscle.

In an operation 50, NMES control signals are determined for driving the NMES pulse generator 32 to generate the NMES pulses at designated anatomical locations r at times (t). In one approach, antagonistic NMES pulses are generated at the same anatomical location as that of the tremor $T(r,t)$. By "antagonistic" it is meant that the NMES pulses induce muscular motion that is opposite that of the tremor. More generally, the appropriate NMES for suppressing tremors may be determined by adaptive training of an artificial neural network (ANN), support vector machine (SVM), or other machine learning (ML) component to tune the NMES response for a specific patient. For example, the ML component can be adaptively trained to produce an NMES that rapidly suppresses the tremor-related EMG signal at the anatomical location of the identified tremor.

However, the approach of generating the NMES pulses at the same anatomical location as that of the tremor may fail to account for tremor migration, which can occur spontaneously or in response to suppression of the tremor. For example, suppression of tremor migration in a distal part of a limb may result in the tremor migration toward a proximal part of the limb.

To address tremor migration, in some embodiments the operation 50 predicts the likely direction (and optionally rate) of tremor migration. In one approach, this is done using an anatomy-specific tremor migration model 52. For example, it is common for a tremor starting in the wrist to migrate proximally toward the elbow or shoulder. Hence, in one embodiment, the anatomy-specific tremor migration model 52 indicates that NMES responsive to a tremor identified in the wrist should be applied to the wrist, the elbow, and shoulder, with progressively lower NMES energy. (This assumes the garment 10 extends over the entire arm including at least a portion of the shoulder, over the elbow and over at least a portion of the wrist. On the other hand, if the garment 10 only covers the wrist through the elbow then the anatomy-specific tremor migration model 52 indicates that the NMES should be applied to the wrist, and the elbow, with lower NMES energy at the elbow compared with the wrist). The anatomy-specific tremor migration model 52 may be implemented based on first principles (e.g., knowledge that the tremor migration is usually in the distal-to-proximal direction for the arm or leg) or by training an ANN, SVM, or other ML component using adaptive training to produce an NMES that rapidly suppresses the EMG signal over the anatomical region (thereby incorporating any tremor migration into the objective function optimized by the ML).

In another approach for addressing tremor migration, the migration can be measured in real time. This takes advantage of the extended length of the garment 10 and the measurement of $EMG(r,t)$ as a function of time. Using the sleeve garment 10 of FIG. 1 as an example, if the tremor initiates near the wrist but then migrates toward the elbow, this would be directly measurable as the $EMG(r,t)$ signal would progressively move up the arm in the direction toward the elbow. The direction and rate of tremor migration is measured, and the NMES is then be applied just ahead of (e.g. just proximal of, in the specific example) the tremor migration front.

Since tremor migration can occur in response to tremor suppression, the applied NMES signal may also be an input to the operation 50, creating a feedback loop where the known location/strength of the NMES is used to predict the likely direction (and possibly also the likely rate) of migration, so that the NMES can be proactively adjusted to suppress the tremor including its expected migration. For example, the applied NMES signal can be an input to the ANN, MVM, or other ML component that is adaptively trained to produce the NMES to rapidly suppress the EMG signal over the anatomical region.

In addition, if the optional IMUs 18 are included, then the output of the IMU readout 26 can be used to determine the orientation 54 of the anatomical region. This, in turn, can be used to more precisely tailor the NMES to suppress the tremors. For the IMU 18 near the wrist in the embodiment of FIG. 1 can be used to determine the pronation/supination of the hand. This can be a further input to the ANN, MVM, or other ML component that produces the NMES, so that the adaptive training takes into account the pronation/supination of the hand.

In some embodiments, the same electrodes 14 are used to detect the EMG signals and also to deliver the NMES. This can be done, for example, if the NMES is delivered as pulses with some dead times between the pulses, and the EMG is measured during the dead times (i.e., time domain multiplexing, TDM, of the EMG detection and NMES delivery is employed). In other embodiments, the electrodes 14 are divided into: a first set of electrodes used to detect the EMG signals; and a second set of electrodes used to deliver the NMES. The electrodes of the two sets are preferably interspersed over the surface area of the anatomical region. While in principle this would allow simultaneous EMG detection and NMES delivery, the NMES is likely to interfere with the EMG detection so that employing EMG detection/NMES delivery TDM is again likely to be beneficial.

In the following, some further aspects are described.

The wearable sleeve can be worn on the arm and includes a) a multitude of electrodes that can record EMG activity of the underlying muscles, b) a multitude of electrodes that can provide transcutaneous electrical stimulation of the muscles (where the EMG recording and stimulation can be done on the same electrodes or on separate electrodes), and optionally c) IMUs for tracking hand/arm position in real time in 3D space.

In another aspect, an NMES system is provided that: 1. can apply stimulation parameters to evoke inhibitory muscle activity or antagonist muscle activity; 2. dynamically adjust stimulation patterns to account for pronation/supination based on IMU data; 3. Further include a nerve stimulation interface that can stimulate the vagus or other nerve branch to affect muscular and/or spinal physiology. Nerve stimulation combined with muscle (i.e. NMES) can potentially further modulate tremor and/or spasticity. The NMES system further includes a control algorithm that can: 1. Take input from the EMG electrodes and IMU sensors on the sleeve; 2. Make decisions based on the inputs to discriminate voluntary movements from tremor induced motion. Note: Most voluntary movements are performed at low (<1 Hz) freq while freq of tremors varies from rest tremor (3-6 Hz), postural tremor (4-12 Hz), kinetic/intention tremor (2-5 Hz or 7 Hz); 3. Decode the type and location of tremor-induced muscle activity; 4. Initiate NMES or nerve stimulation to minimize the effects of tremor by stimulating the inhibitory muscle activity or antagonist muscle activity; 5. Take into account the distal to proximal migration of tremors under attenuation to optimize tremor attenuation.

Advantageously, tremor migration can be detected by a combination of EMG and/or IMU data. Therefore, a strategy can be employed to overcome tremor migration by slowly ramping up stimulation amplitude and changing stimulation pattern or optimizing stimulation parameters such as freq, pulse width etc. A genetic algorithm-based approach may be used to minimize the error between the desired state and current state.

In yet another aspect, an oscillator (such as a Matsuoka oscillator) model may be used to generate rhythmic/oscillatory output to enable stimulation of rhythmic muscle activity to overcome cyclic tremor oscillations.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A tremor suppression device comprising:
   a garment wearable on an anatomical region and including electrodes contacting the anatomical region when the garment is worn on the anatomical region; and
   an electronic controller configured to:
   detect electromyography (EMG) signals as a function of anatomical location and time using the electrodes;
   identify tremors as a function of anatomical location and time based on the EMG signals;
   determine tremor suppressing neuromuscular electrical stimulation (NMES) at one or more anatomical locations as a function of time based on the identified tremors and an anatomy-specific tremor migration model; and
   apply the determined tremor suppressing NMES using the electrodes to suppress the identified tremors.

2. The tremor suppression device of claim 1, wherein the electronic processor is configured to identify tremors by operations including spectral filtering the EMG signals to remove frequency components corresponding to voluntary motion.

3. The tremor suppression device of claim 1, wherein the determining of the tremor suppressing NMES is further based on the applied tremor suppressing NMES creating a feedback loop to adjust the applied tremor suppressing NMES.

4. A tremor suppression device comprising:
   a garment wearable on an anatomical region and including electrodes contacting the anatomical region when the garment is worn on the anatomical region; and
   an electronic controller configured to:
   detect electromyography (EMG) signals as a function of anatomical location and time using the electrodes;
   identify tremors as a function of anatomical location and time based on the EMG signals;
   determine a tremor migration rate and direction based on a rate of change in anatomical location of the identified tremors as a function of time;
   determine tremor suppressing neuromuscular electrical stimulation (NMES) at one or more anatomical locations as a function of time based on the identified tremors and the determined tremor migration rate and direction; and
   apply the determined tremor suppressing NMES using the electrodes to suppress the identified tremors.

5. The tremor suppression device of claim 4, wherein the electronic processor is configured to identify tremors by operations including spectral filtering the EMG signals to remove frequency components corresponding to voluntary motion.

6. The tremor suppression device of claim 4, wherein the determining of the tremor suppressing NMES is further based on the applied tremor suppressing NMES creating a feedback loop to adjust the applied tremor suppressing NMES.

* * * * *